(12) United States Patent
Ausserer et al.

(10) Patent No.: US 7,169,277 B2
(45) Date of Patent: Jan. 30, 2007

(54) HIGH THROUGHPUT SEPARATIONS BASED ANALYSIS SYSTEMS

(75) Inventors: Walter Ausserer, San Carlos, CA (US); Luc J. Bousse, Los Altos, CA (US); Robert S. Dubrow, San Carlos, CA (US); Steven A. Sundberg, San Francisco, CA (US); Andrea W. Chow, Los Altos, CA (US); Benjamin N. Wang, Palo Alto, CA (US)

(73) Assignee: Caliper Life Sciences, Inc., Mountain View, CA (US)

( * ) Notice: Subject to any disclaimer, the term of this patent is extended or adjusted under 35 U.S.C. 154(b) by 552 days.

(21) Appl. No.: 09/919,505

(22) Filed: Jul. 31, 2001

(65) Prior Publication Data

US 2002/0033337 A1 Mar. 21, 2002

Related U.S. Application Data

(60) Provisional application No. 60/327,566, filed on May 17, 2001, provisional application No. 60/276,731, filed on Mar. 16, 2001, provisional application No. 60/222,491, filed on Aug. 2, 2000.

(51) Int. Cl.
*G01N 27/26* (2006.01)
(52) U.S. Cl. .................. 204/453; 204/455; 204/604; 204/605
(58) Field of Classification Search ........ 204/451–455, 204/601–605; 210/656–659, 635
See application file for complete search history.

(56) References Cited

U.S. PATENT DOCUMENTS 4,486,311 A * 12/1984 Nakajima et al. ........... 210/635
5,699,157 A    12/1997 Parce
5,779,868 A     7/1998 Parce et al.
5,846,727 A * 12/1998 Soper et al. ................. 435/6
5,852,495 A    12/1998 Parce
5,955,028 A     9/1999 Chow
5,976,336 A    11/1999 Dubrow et al.
6,010,607 A *  1/2000 Ramsey ..................... 204/435

(Continued)

FOREIGN PATENT DOCUMENTS

WO    WO 98/49548    * 11/1998

(Continued)

OTHER PUBLICATIONS

Schmalzing, D. et al., "DNA typing in thirty seconds with a microfabricated device," PNAS (1997) 94:10273-10278.

(Continued)

*Primary Examiner*—Nam Nguyen
*Assistant Examiner*—Jeffrey Barton
(74) *Attorney, Agent, or Firm*—Donald R. McKenna; Ann C. Petersen

(57) ABSTRACT

Devices, systems and methods for use in separating sample materials into different fractions that employ bulk fluid flow for loading of samples followed by electrophoretic separation of the sample material. Devices employ configurations that optionally allow bulk sample loading with some or no displacement of a separation matrix within a separation conduit. Methods of using these devices, and systems that incorporate these devices are also envisioned.

27 Claims, 10 Drawing Sheets

U.S. PATENT DOCUMENTS

| | | |
|---|---|---|
| 6,012,902 A | 1/2000 | Parce |
| 6,042,709 A | 3/2000 | Parce et al. |
| 6,043,080 A | 3/2000 | Lipshutz et al. |
| 6,068,752 A | 5/2000 | Dubrow et al. |
| 6,071,478 A | 6/2000 | Chow |
| 6,080,295 A | 6/2000 | Parce et al. |
| 6,153,073 A | 11/2000 | Dubrow et al. |
| 6,207,031 B1 * | 3/2001 | Adourian et al. ........... 204/451 |
| 6,233,048 B1 | 5/2001 | Parce |
| 6,235,175 B1 | 5/2001 | Dubrow et al. |
| 6,274,089 B1 | 8/2001 | Chow et al. |
| 6,287,520 B1 | 9/2001 | Parce et al. |
| 6,375,817 B1 * | 4/2002 | Taylor et al. ............... 204/453 |

FOREIGN PATENT DOCUMENTS

| | | |
|---|---|---|
| WO | WO 99/39190 | 8/1999 |
| WO | WO 00/43766 | 7/2000 |
| WO | WO 00/45172 | 8/2000 |
| WO | WO 00/46594 | 8/2000 |
| WO | WO 00/63704 | 10/2000 |

OTHER PUBLICATIONS

Woolley, A.T. et al., "Ultra-high-speed DNA fragment separations using microfabricated capillary array electrophoresis chips" *PNAS* (1994) 91:11348-11352.

* cited by examiner

> US 7,169,277 B2

HIGH THROUGHPUT SEPARATIONS BASED ANALYSIS SYSTEMS

RELATED APPLICATIONS

This application claims priority to U.S. Provisional Patent Application Nos. 60/327,566, filed May 17, 2001, 60/222, 491, filed Aug. 2, 2000, and 60/276,731, filed Mar. 16, 2001. The entire disclosure of each of these applications is hereby incorporated herein by reference in its entirety for all purposes.

BACKGROUND OF THE INVENTION

Separations based analyses are a prominent part of biological research, allowing one to characterize different biological samples, reaction products and the like. Examples of some of the more prevalent separations based analyses include electrophoretic separations of macromolecular species, e.g., proteins and nucleic acids. While conventional technologies have been developed that are able to perform these separations based analyses, and in some cases at reasonably high rates, these systems still suffer from slower than optimal throughput and labor intensive operation. For example, conventional slab gel electrophoresis is a very time consuming and labor intensive process where samples are electrophoretically separated in a flat slab gel, a process that can take from one to several hours. The gel and its included samples must then be stained and destained in order to detect the separated species within the gel. Again, the staining and destaining process can take several hours to complete. Capillary systems have also been developed that are generally automatable but still require long run times in order to achieve suitable separations.

Microfluidic devices have also been applied in separations based analyses, and have yielded substantial advantages in speed and accuracy. Despite these advantages, however, commercially available microfluidic separations systems have not yet achieved the throughput that is generally desired. Accordingly, it would be extremely useful to provide analytical systems and methods that have improved throughput, as well as accuracy and automatability. The present invention meets these and a variety of other needs.

BRIEF SUMMARY OF THE INVENTION

The present invention generally provides channel based systems that integrate bulk material movement and electrokinetic separations in a single analytical unit. This is typically in the form of bulk loading of a fluid that contains a sample material of interest, followed by the electrophoretic separation of the constituent components of that sample material.

In a first aspect, the invention provides methods of separating a sample material into a plurality of fractions, by providing a system that includes a separation conduit having a separation matrix disposed therein and a sample loading conduit in fluid communication with the separation conduit at an intermediate point along the sample loading conduit. The method comprises bulk flowing a sample material into the sample loading conduit without substantially displacing the separation matrix from the separation conduit, followed by injecting a portion of the sample material into the separation conduit. Injected sample materials are then separated into a plurality of fractions.

In a related aspect, the present invention also provides a method similar to that described above, except wherein a portion, but not all of the separation matrix within the separation conduit is replaced between sample material separations, e.g., prior to and/or following a particular separation.

The present invention also provides methods of separating a sample material into a plurality of fractions, by providing a system that includes a separation conduit having a separation matrix disposed therein, a sample loading conduit in fluid communication with the separation conduit, a source of sample material in fluid communication with the sample loading conduit, and a source of first reagent in fluid communication with the sample loading conduit. The sample material and the first reagent are transported into the sample loading conduit, so that the sample material and first reagent form a first mixture. A portion of the first mixture is injected into the separation conduit; and the sample material in the portion of the first mixture is separated into a plurality of fractions.

Relatedly, the present invention provides a separation system, that comprises a separation conduit having a first fluidic resistance and a flowable separation matrix disposed therein. The system also includes a sample loading conduit fluidly connected to the separation conduit and having a second fluidic resistance, and a sample loading system for transporting a sample material into the sample loading conduit. The first fluidic resistance is higher than the second fluid resistance by an amount sufficient to prevent substantial displacement of the separation matrix when sample material is transported into the sample loading conduit.

In a similar aspect, a separation system is provided that comprises a separation conduit having a flowable separation matrix disposed therein, a sample loading conduit fluidly connected to the separation conduit, a source of sample material in fluid communication with the sample loading conduit, and a source of a first reagent in fluid communication with the sample loading conduit by a first reagent introduction channel. A pressure or vacuum source is then coupled to the sample loading conduit for applying a pressure difference across the sample loading conduit, wherein the sample loading conduit and first reagent introduction channel are dimensioned to transport sample material and first reagent into the sample loading conduit at a preselected ratio under the applied pressure difference.

DETAILED DESCRIPTION OF THE INVENTION

I. General Aspects of the Invention

Figure 1A:
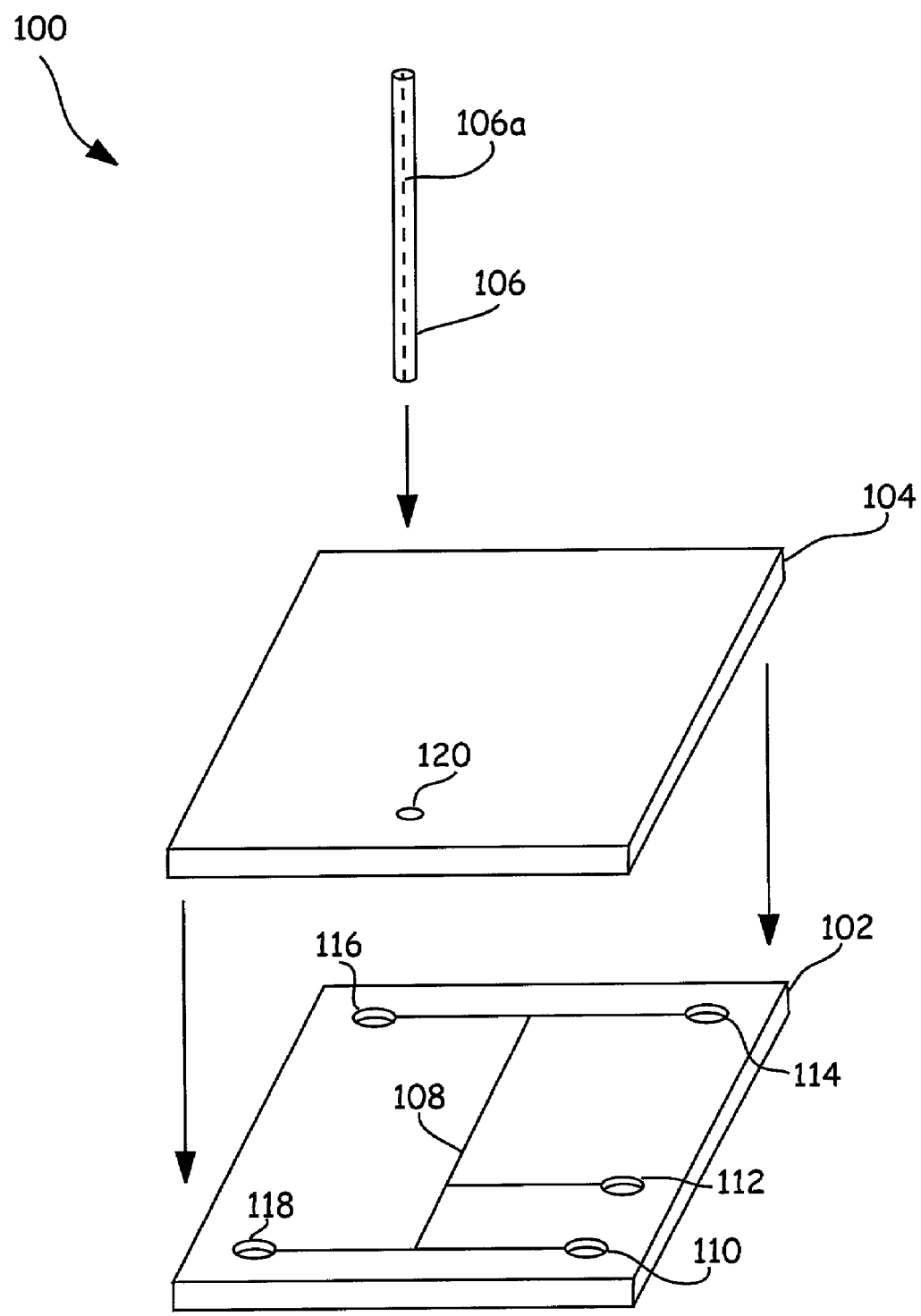
FIGS. 1A and 1B schematically illustrate a layered construction for a microfluidic channel containing device.

The present invention is generally directed to improved methods and systems for performing analytical operations that include a separation function, e.g., employing a separation matrix. In particular, these methods and systems are particularly suited for high throughput separations based analyses, e.g., nucleic acid separations, protein separations, or the like.

In particular, the methods and systems of the present invention gain substantial speed of throughput by loading individual samples via a bulk fluid loading process where sample material is flowed into a loading conduit. Sample loading is followed by separation of a portion of the sample material in a separation conduit fluidly connected to the loading conduit, e.g., via electrophoretic separation. Because samples are bulk flowed into the loading conduit, samples can be efficiently loaded, in series, for serial analysis in the separation conduit.

In bulk loading of fluids in interconnected conduits, there is a tendency for fluids to flow or be pushed into the various interconnected conduits. In the case of the systems described herein, it is often desirable to avoid bulk flow of sample materials into the separation conduit to avoid uncertainties in the amount of sample material analyzed, and to avoid substantially displacing any separation matrices that are used in the separation conduit. Accordingly, in the context of the present invention, the system is generally configured so as to permit such bulk fluid flow through the sample loading conduit while not substantially displacing any separation matrix within the separation conduit, or displacing such matrix to a partial and/or preselected degree.

The present invention also provides for simultaneous loading of sample materials while intermixing such materials with additional reagents, such as marker compounds, e.g., molecular weight standards, labeling compounds, diluents, and the like. By combining the reagent mixing step with the loading function, one eliminates additional sample preparation steps of dilution, internal standard addition, etc., that are typically carried out separately from the separation system, e.g., in multiwell plates.

A number of additional features are optionally included with the systems described herein for particular operations and manipulations, and these are generally described in greater detail below.

II. Systems

In accordance with the present invention, systems are provided for use in performing separations based analytical operations. As such, these systems typically employ a separation conduit that has disposed therein a separation matrix. A sample loading conduit is provided that is fluidly connected to the separation conduit to permit delivery of a sample material to the separation conduit wherein the separation operation, and typically detection, portion of the analysis takes place. The sample and separation conduits may take a variety of different forms, including simple tubing or capillaries joined together to form the interconnected conduits described herein. However, in preferred aspects, such systems are embodied within an integrated body structure or microfluidic device, wherein the conduits are fabricated in a monolithic substrate.

Typically, such body structures are fabricated in a layered structure where a first planar substrate is manufactured to include one or more grooves etched, carved, embossed, molded, or otherwise manufactured into a planar surface of the substrate. These grooves typically define the layout of at least a portion of the interconnected channel network of a microfluidic device's body structure. A second substrate layer is then overlaid and bonded to the planar surface of he first substrate to sealably enclose the grooves, and thereby define the enclosed conduits or channels of the device.

Figure 1B:
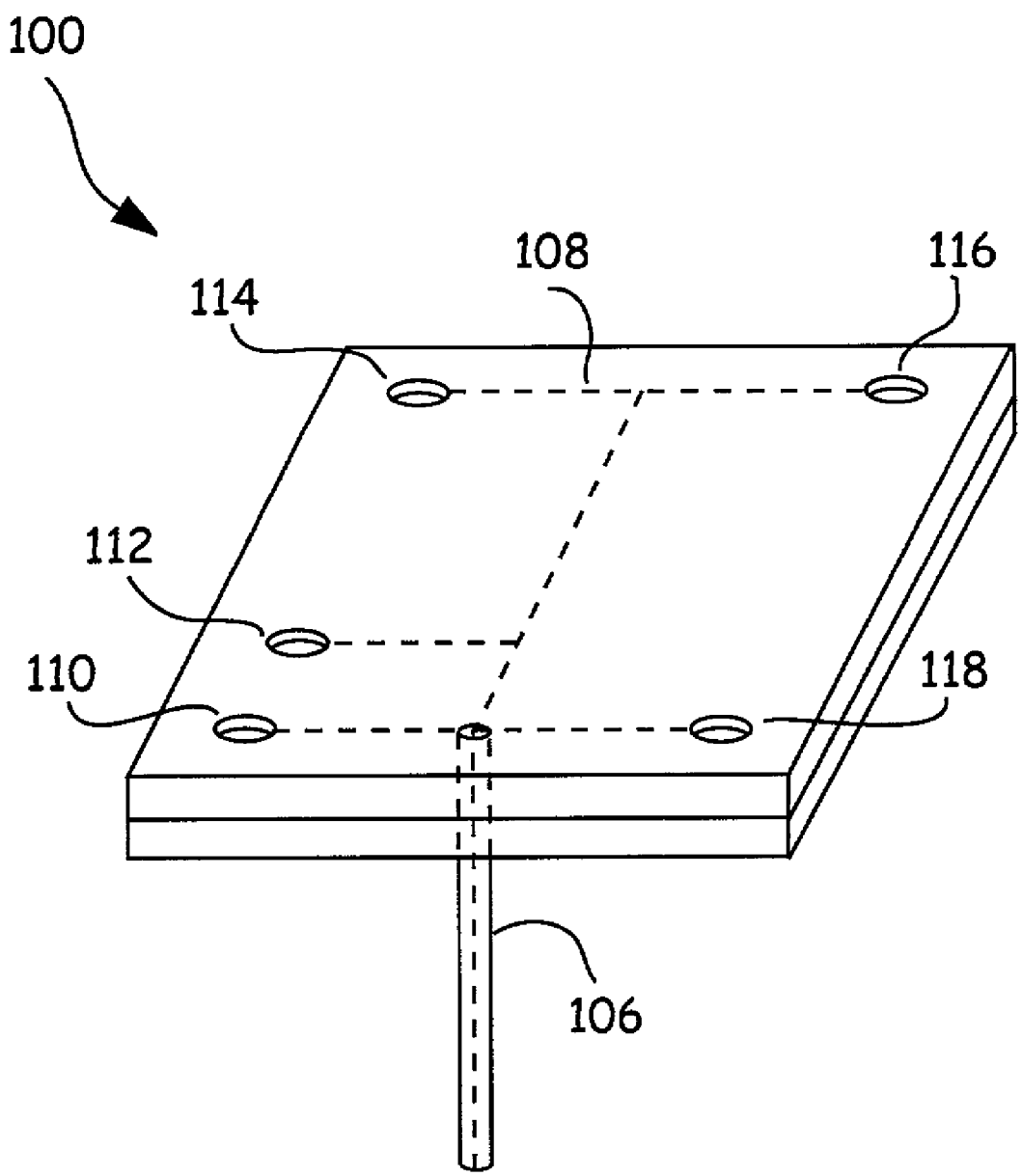

A schematic illustration of the layered construction of a simplified microfluidic device is shown in FIG. 1A. The illustrated device is shown inverted as compared to normal operation for ease of illustration. As shown, the overall device 100 is fabricated from two planar substrate layers 102 and 104. The device illustrated also includes a sampling element or capillary 106 that is attached to the finished structure. In fabricating the device shown, a network of grooves 108 is fabricated into the surface of substrate 102. The grooves can be fabricated into a variety of different configurations or network geometries depending upon the type of operation to which the device is to be put. As shown, each groove terminates in an aperture or port disposed through substrate 102, e.g., ports 110–118. When substrates 102 and 104 are mated together and bonded as indicated by the arrows, the groove network is sealed to define an enclosed channel network. The ports 110–118 are sealed on one side to define fluid reservoirs and access points to the channel network. Capillary element 106 is inserted and attached through aperture 120, which is positioned such that the channel 106a disposed within capillary 106 will be in fluid communication with the channel network 108. An assembled, properly oriented device is illustrated in FIG. 1B.

In accordance with the present invention, both the separation and sample loading conduits or channels are provided substantially within the integrated body structure. In particularly preferred aspects, these conduits are of microscale dimensions, meaning that they have at least one cross-sectional dimension that is less than 500 µm, e.g., between about 0.1 and about 500 µm, and preferably between about 1 µm and about 200 µm, and more preferably between about 1 µm and about 100 µm. Such integrated devices typically provide numerous advantages over previously described systems as a result of their precise tolerances and the accuracy with which their operations can be controlled.

The sample-loading conduit, in addition to being in fluid communication with the separation conduit, is also in fluid communication with at least a first source of sample material. In the case of an integrated body structure, the source of sample material may be integrated with the body structure, e.g., as one or more reservoirs disposed in the body structure and in fluid communication with the loading channel. Alternatively, the source of sample material may be external to the body structure, e.g., a test tube, or well in a multiwell plate, which is placed into fluid communication with the sample loading conduit via a sampling pipettor or capillary element which is itself connected to or a part of the sample loading channel.

Figure 2A:
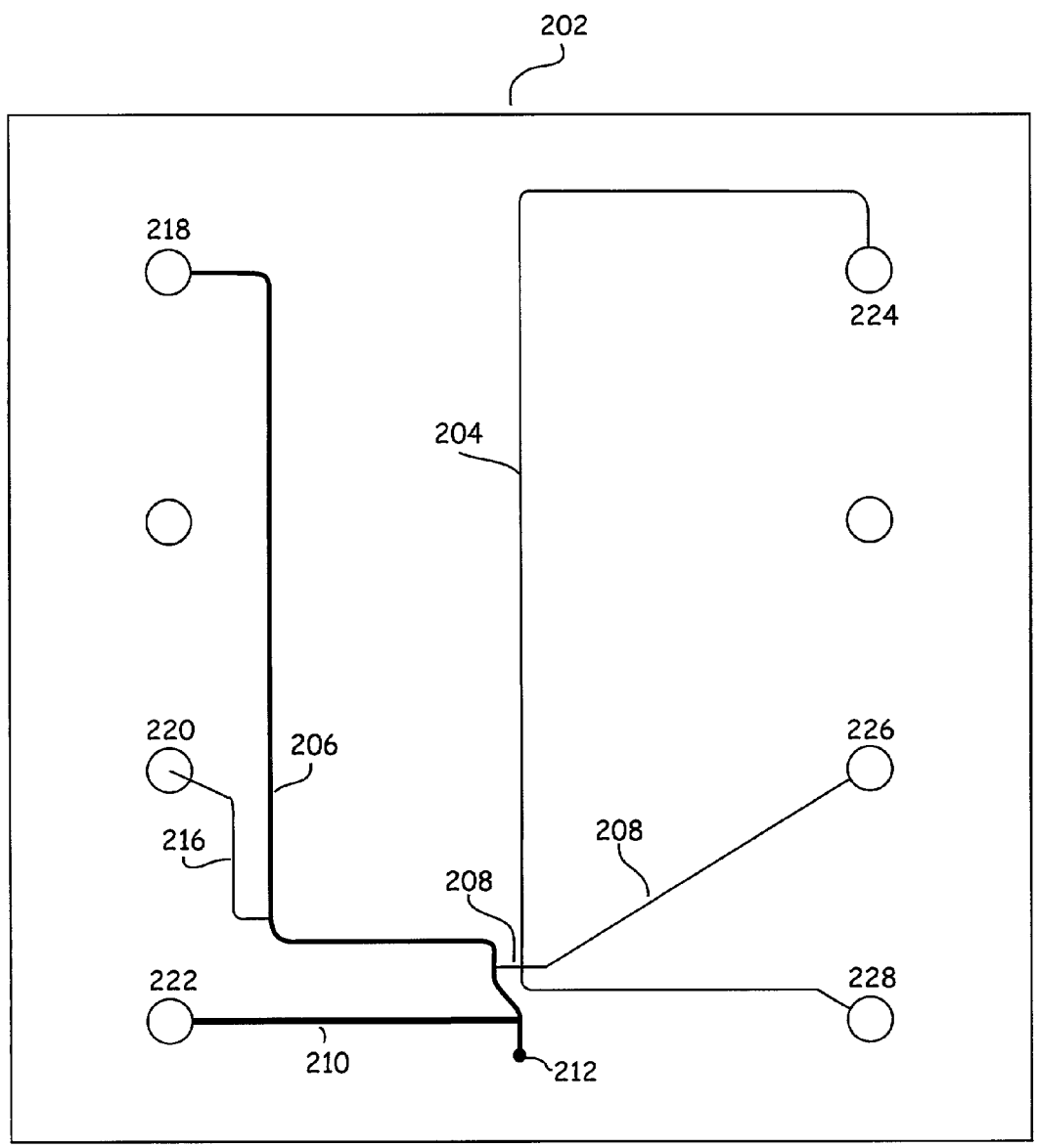
FIG. 2A is a channel layout for a microfluidic device that is particularly suited for performing the separations based analyses of the present invention.
Figure 2B:
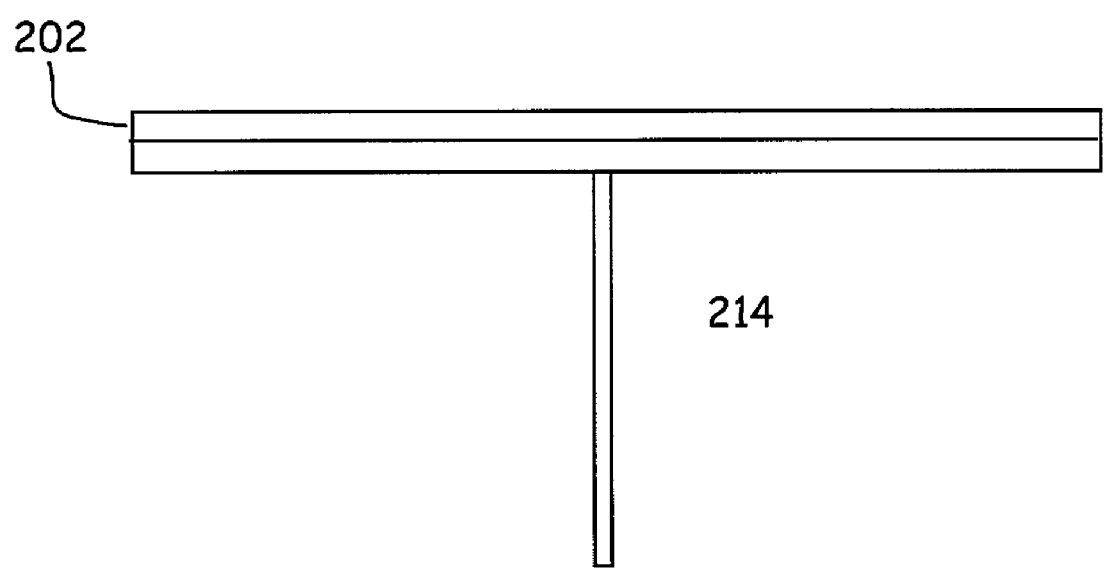
FIG. 2B illustrates a side view of the microfluidic device of FIG. 2A.

Examples of integrated devices including a sample loading conduit and separation conduit are illustrated in FIGS. 2A and 2B. As shown, the device 200 includes a main body structure 202. The body structure 202 houses a separation channel 204 and at least a portion of a sample loading channel 206. As shown, the overall sample loading channel 206 includes an external sampling pipettor 214 (in FIG. 2B) or capillary, having a capillary channel or conduit disposed therethrough, which communicates with channel 206 via port 212. The pipettor 214 is open at one end so as to be able to access sample materials from external storage vessels, e.g., test tubes, multiwell plates, etc. Alternatively, sample loading channel may be provided in communication with one or a plurality of different sample material reservoirs (not shown) that are integral to the device's body structure 202, in place of the external sampling pipettor 214. Sampling pipettors for microfluidic devices are described in detail in U.S. Pat. No. 5,779,868, which is incorporated herein by reference in its entirety for all purposes.

As shown, separation channel 204 is in communication with a buffer reservoir 228 at one end and at a waste reservoir 224 at the other end. In addition to providing reservoirs for buffer, separation matrix and waste materials following analysis, these reservoirs also provide electrical access for electrophoretic separations. Specifically, electrodes are placed into contact with fluids in, e.g., reservoirs 224 and 228, in order to apply the requisite current through the separation channel 204 to electrophoretically separate the sample material into various fractions, or constituent elements. Similarly, sample loading channel 206 is fluidly connected at one end to the sampling pipettor 214 (or to one or a plurality of sample reservoirs (not shown)), and at the other end to a waste reservoir 218. The waste reservoir 218 optionally provides an access port for a vacuum source to draw sample materials into the sample loading channel 206 via bulk fluid flow. In certain cases, bulk flow of sample materials and/or other reagents may be driven either by application of a vacuum to the waste reservoir 218, or by application of positive pressure to the sample material or reagent reservoirs, or a combination of the two.

As shown, the sample loading channel 206 is connected to the separation channel 204 via a injection channel 208, which forms a fluid junction between the sample loading channel and the separation channel, which, as shown, intersects the sample loading channel 206 near one terminus, crosses the separation channel 204, and is connected to a reservoir 226 at its other terminus. Although illustrated as residing at intermediate points in both the sample loading channel and the separation channel, the fluid junction represented by channel 208 could optionally be provided at a terminus of one or both of these channels, depending upon the desired application.

As in the case of the separation and sample loading channels, the illustrated reservoir optionally provides storage for buffers and/or waste materials, and also provide access to the channels of the device to control movement of material from the sample loading channel 206 into the separation channel 204 (also termed "injection" of the sample material).

Optionally, one or more additional reagent reservoirs, e.g., reservoir 222, may be provided within the integrated body structure 202 of the device 200. These additional reservoirs provide additional reagents that may be used in the analytical operation that is to be carried out. Examples of such reagents include, e.g., internal standards, e.g., molecular weight markers for size based separations, labeling compounds, e.g., intercalating dyes, affinity labels, or the like, diluents, buffers, etc. The reagent reservoir 222 is fluidly connected to the sample loading channel 206 via a reagent introduction channel 210.

Additional reservoir 220 is also provided fluidly connected to sample loading channel 206 via channel 216. In the device shown, this additional reservoir and channel are used to apply the necessary motive force to inject sample material from sample loading channel 206, through the injection channel 208, and into separation channel 204. In the case of an electrokinetic injection, this is accomplished by applying a current between reservoir 220 and reservoir 226 so as to electrokinetically move material through the intersection of injection channel 208 and separation channel 204. Similarly, a pressure differential is optionally applied between these reservoirs in order to bulk flow sample material through that intersection. Where bulk flow is used to inject, pressures are preferably simultaneously adjusted at each of the reservoirs (as well as the pipettor) to ensure that flow through the intersection occurs in a controlled manner, e.g., without excessive flow into the main portions of the separation channel.

Additional post separation reactions are also optionally performed in accordance with the methods and systems described herein, including post separation labeling, dilution, heating, or the like. Such post separation treatments typically involve the addition of reservoirs and channels connected to the separation channel near the waste reservoir end, but before a detection zone within the channel. In certain preferred aspects, e.g., in protein separations, a post separation dilution step is employed to dilute out the amount of detergent, i.e., SDS, to below a critical micellar concentration, in order to optimize the detection of labeled proteins versus the free detergent micelles. Such post column treatments are described in detail in published PCT Application No. WO 00/46594, and incorporated herein by reference in its entirety for all purposes. An example of a microfluidic device incorporating a channel geometry for carrying out such post separation reactions is illustrated in FIG. 3C.

In addition to the microfluidic device, the systems of the invention optionally include additional components, such as flow controllers for bulk flowing sample materials into the sample loading channel, electrical controllers for applying currents through the separation channels (and optionally the injection channels), and detection systems for detecting separated sample material fractions.

Flow controllers typically include one or more variable or constant pressure or vacuum sources along with an interface for operably coupling the sources to the reservoirs. Such interfaces typically include ports with sealing gaskets, O-rings, insertion couplers, or the like, for providing a sealed connection between the pressure or vacuum source and the reservoir or port. The pressure or vacuum sources may apply a fixed or variable pressure, depending upon the particular operation that is to be performed. Fixed and variable pressure and vacuum sources are well known and include, e.g., peristaltic pumps, syringe pumps, diaphragm pumps, and the like. The pressure and/or vacuum sources are typically coupled to one or more different reservoirs on a device to control pressures at one or more reservoirs. Examples of multi-reservoir independent pressure controllers are described in, e.g., U.S. Patent Application No. 60/184,390, filed Feb. 23, 2000, and incorporated herein by reference in its entirety for all purposes. Bulk fluid control is also optionally controlled using electrokinetic forces, e.g., electroosmosis, through the inclusion of integrated or external electroosmotic pumping systems. Examples of electroosmotic pumps are described in U.S. Pat. No. 6,012,902, which is incorporated herein by reference in its entirety for all purposes. A variety of other bulk fluid flow methods are also optionally used in practicing the present invention. For example, centrifugal forces may be employed to direct fluid movement where channel networks are fabricated into a rotor shaped body, where the direction of flow extends radially outward from the center of the rotor. Similarly, wall shear methods can be used to bulk flow fluids, e.g., by moving two opposing surfaces relative to each other. Capillary forces are also optionally employed to cause bulk fluid movement in channel networks (see, e.g., published PCT Application No. WO 00/43766, which is incorporated herein by reference in its entirety). Other bulk fluid flow methods include gas generation techniques or fluid/gas expansion/contraction methods based upon temperature changes, see, e.g., U.S. Pat. No. 6,043,080 to Lipshutz et al., which is also incorporated herein by reference in its entirety for all purposes.

In addition to controlling bulk fluid flow during the sample loading process, the systems of the present invention also include controller aspects for controlling the injection of sample material into the separation conduit as well as moving sample materials through the separation conduit to accomplish the desired separation/fractionation. As noted above, the injection and separation operations are optionally carried out using pressure based or bulk fluid movement methods, e.g., sample is injected using pressure and separated through an appropriate separation matrix using pressure-based or bulk flow of the fluid containing the sample materials. In such cases, the bulk flow controllers described above are simply expanded to control flow within these additional portions of the microfluidic device. In preferred aspects, however, at least one of the injection and separation operations are carried out by the electrophoretic movement of sample materials, e.g., in the absence of substantial bulk flow.

In such cases, the controllers for these operations typically include electrical power supplies coupled via appropriate circuitry to an electrical interface that delivers electrical current through the appropriate conduits of the system, e.g., the injection and/or separation conduits. Typically, these interfaces comprise electrode pins that are positioned on the interface component of the controller to be inserted into the reservoirs of the device. However, optionally, the interfaces comprise electrical contacts, e.g., contact pads, insertion couplers, or the like, that interface with electrical contacts on the body structure of the device that includes the separation conduit. These contacts then deliver current through the appropriate conduits via electrical circuitry disposed on or within the body structure, which circuitry delivers voltages to reservoirs or conduits. Examples of different interfacing scenarios are described in U.S. Pat. No. 5,955,028, which is incorporated herein by reference in its entirety for all purposes.

In addition to control components, the systems of the present invention also typically include detection systems for detecting the separated fractions of the sample material within the separation channel, i.e., following separation. Detection systems may be based upon a variety of well known detection methods, including fluorescence spectroscopy (laser induced and non-laser methods), UV spectroscopy, electrochemical detection, thermal detection, capacitance based detection (see Published PCT Application No. WO 99/39190), mass spectrometry based detection, e.g., MALDI-TOF and electrospray, which can be readily configured to receive materials directly from capillary or microfluidic device outlets, and the like. In preferred aspects, optical detection methods, and particularly fluorescence based detection methods are used. Such detection systems generally include an excitation light source that provides light at an appropriate wavelength to excite the particular fluorescent species that is to be detected. The excitation light is then transmitted through an appropriate optical train, including lenses, filters (e.g., wavelength and/or spatial filters), beam splitters, etc., and directed through, e.g., an objective lens, at a translucent portion of the separation conduit. As fluorescent species, constituents or fractions of the sample material pass through the excitation light, they fluoresce. The fluorescent emissions are then collected and transmitted back through the objective lens and the same or an alternate optical train to a light sensor, e.g., a photodiode, photomultiplier tube, CCD or the like.

The systems also typically include a processor, e.g., a computer, that is programmed to record the data received from the detectors, and optionally analyze the data, e.g., integrate peaks, calculate retention times, calibrate separations with internal standards, etc. The processor is also preferably programmed to monitor and instruct the operation of the controllers in accordance with a set of preprogrammed and/or user input instructions, e.g., how fast to bulk flow or electrophoretically move materials, positions in sample source arrays from which samples should be taken, e.g., wells in a microplate, etc.

A number of other components are also optionally added to the systems described herein depending upon the particular applications that are being performed, including, e.g., temperature control element, e.g., heating and cooling elements for heating and/or cooling portions of the devices described herein, robotic components for moving sample plates and/or devices around to access different materials and/or functionalities of the overall system. In general, all of these additional components are commercially available and are readily adapted to the systems described herein.

A schematic illustration of an overall system, as described above, is shown in FIG. 4. As shown, the system includes a microfluidic device 400, e.g., as illustrated in FIGS. 2 and 3. The microfluidic device 400 is typically operably coupled to a flow controller system 402. This flow controller 402 applies appropriate motive forces to the materials within the channels of the device 400 to carry out a desired operation. In accordance with the preferred methods described herein, and with reference to FIGS. 2 and 4, the controller 402 generally includes a pressure and/or vacuum source, as well as an electrical power supply. The electrical power supply is coupled to the channels of the device through which electrokinetic movement is desired, e.g., injection channel 208 and separation channel 204, via reservoirs 220 and 226, 224 and 228, respectively, e.g., using electrical connectors 408 which are connected to or are themselves, the electrodes that are disposed in the reservoirs to contact the fluid therein. The pressure/vacuum source is typically coupled to the channels through which pressure induced bulk flow is desired, e.g., channel 206 and/or 222, and/or capillary element 214. In the case of the preferred aspects of the present invention a single vacuum source is generally connected to reservoir 218 via vacuum line 410, to draw material into and through channel 206 from the capillary element (and thus, any sample sources into which the capillary was placed), as well as reagent reservoir 222. As noted, electrical coupling is generally carried out via electrodes that are connected to the power supply and dipped into the reservoirs of the device. Pressure/vacuum connections typically involve the use of a sealing pressure connection, e.g., that employs a gasket or o-ring, to communicate pressure to a reservoir, which is schematically illustrated as connector 412. In general, these types of instrument/device interfaces are described in U.S. Pat. Nos. 5,955,028, and 6,071,478, each of which is incorporated herein by reference in its entirety for all purposes. Pressure or vacuum sources are generally widely available and will vary depending upon the needs of a particular application. Typically, for microfluidic applications, positive displacement pumps, e.g., syringe pumps and the like, are employed as pressure or vacuum sources. A variety of other pumps including peristaltic, diaphragm and other pumps are as readily employed.

A detector 404 is also typically employed in the overall system. The detector is typically placed within sensory communication of one or more of the channels of the device. As used herein, the phrase "within sensory communication" refers to positioning of a detector such that it is capable of receiving a detectable signal from the contents of a channel. In the case of optical signals, this only requires that the detector be positioned to receive optical signals from the material within a channel. This is generally accomplished by positioning an optical detector adjacent to a transparent or translucent portion of a channel segment such that it can receive the optical signal. Optical detectors are generally well known in the art and include fluorescence based detectors (intensity and polarization), spectrophotometric detectors, optical scattering detectors, and the like. For other detection schemes, e.g., electrochemical detection, the detector, or a portion of the detector is often placed into physical contact with the fluids within the channel containing device, e.g., via electrodes, semiconductor based sensors or microelectromechanical sensors (MEMS). Alternate detectors are also optionally employed in the methods described herein, including out-of-channel detection schemes, e.g., mass spectrometry based detection, through MALDI-TOF or electrospray mass spectrometry methods. These detection schemes also have been previously described.

In addition to detector 404, controller 402 and device 400, an overall system typically includes a computer or processor 406, which is operably coupled to controller 402 and detector 404. The computer is typically connected both to the detector 404 and the controller 402. The computer typically includes programming to instruct the operation of the controller to direct fluid movement through the channels of the device 400 in accordance with user specified instructions. Additionally, computer 406 also is programmed to receive and record data from detector 404 and optionally analyze the data and produce a user comprehensible output or report.

Systems optionally employ sample accessing systems, e.g., robotic x-y-z translation stages and other multiwell plate handling equipment for delivering a sample material well to the sampling element of a microfluidic device, e.g., so that the capillary can be immersed in a sample material, and access multiple different wells on a single plate as well as multiple plates. Commercially available systems include, e.g., Carl Creative conveyor systems, as well as Twister systems available from Zymark Inc. and robotic x-y-z translation arms, e.g., as available from Parker Positioning Systems, Inc.

III. Pressure Loading/Electrophoretic Separations

As noted above, the present invention is directed, at least in part, to devices, systems and methods of performing separation based analyses where the material to be analyzed ("sample material") is loaded into a sample loading conduit via bulk fluid flow, and then subjected to separation through a separation matrix either via pressure based chromatography, e.g., forcing the sample material through an appropriate separation matrix (exclusion, affinity, ion exchange, hydrophobic/hydrophilic, or the like) or by electrophoresis. The phrase bulk flow, as used herein, refers to the movement of fluid through a particular space, which fluid movement carries with it any suspended or dissolved constituents of the fluid. This is in contrast to the movement of these individual constituents through the fluid, independent of the movement of the fluid itself, e.g., as in electrophoresis.

The features and operation of the present invention are readily illustrated with reference to the device shown in FIG. 2 and described above. Initially, a separation matrix is introduced into or is already associated with the separation channel 204, e.g., coated during fabrication. Where a separation matrix is introduced into the separation channel, it is generally placed into one of reservoirs 224 or 228 and allowed to wick into the separation channel, with or without additional applied pressure. Typically, separation matrices are provided as liquid media or slurries of solid phase media, e.g., beads. Examples of preferred electrophoretic separation matrices include polymeric solutions, e.g., linear polyacrylamides, hydroxycellulose polymers, and the like. In preferred aspects, separation matrix is added to the separation channel of the device prior to adding any additional fluid components. Buffers and other fluids are then added to the appropriate channels of the device by pressure flow, which forces the matrix out of those channels. Alternatively, separation matrix may be added after the entire system is filled with a buffer, e.g., by bulk flowing the matrix primarily into the separation channel.

Sample material is then drawn into the sample loading channel 206, e.g., by placing the external pipettor 214 into contact with a source of sample material and drawing the material through the pipettor 214 and sample loading channel 206. During the sample loading process, any separation matrix that has entered the sample loading channel 206 is washed away by the bulk flow of the sample material.

As the sample loading channel 206 is connected to the separation conduit 204 and loaded by bulk flow, the system is generally configured such that the bulk loading of the sample material does not adversely affect the separation conduit 204, or its contents, e.g., by forcing sample material into the separation channel, prematurely, or displacing the separation matrix to a substantial extent, e.g., either by pushing the matrix out of the channel or pulling it into the sample loading channel. As will be clear based upon the following discussion, a certain amount of displacement is often tolerated in these systems, and in fact can be desirable in some instances.

In particular, a sample material is bulk flowed into sample loading channel 206. As noted above, in one aspect, the sample material is drawn into the sample loading channel via an external sampling capillary 214, or optionally from one or more integrated sample material reservoirs (not shown). Drawing a sample material into the sample loading channel is typically carried out by applying a negative pressure (or vacuum) to reservoir 218 to draw sample material into and through the sample loading channel. Channels may include additional elements that aid in the performance of a desired operation, including, e.g., surface coatings for reducing media/wall interactions, electroosmotic flow, etc.

As shown, the device 200 also includes at least a first reagent introduction channel 210 that fluidly couples a first reagent reservoir 222 to the sample loading channel 206. When the sample material is drawn into the sample loading channel 206, additional reagent is also introduced into the sample loading channel 206 from reservoir 222. Specifically, when a vacuum is applied to draw sample material into the sample loading channel 206 through capillary 214, it simultaneously draws in reagent from reagent reservoir 222 via channel 210, which then mixes with the sample material. The desired ratio of sample material and additional reagent (s) can be achieved by appropriately configuring the ratio of flow resistances of the channels through which materials are being introduced into a common channel, e.g., the junction of the sample loading channel 206, reagent introduction channel 210 and capillary 214. For example, by providing the reagent introduction channel 210 with a flow resistance equivalent to that of the sampling capillary 214, one will achieve substantially equal mixing of reagent and sample material within the sample loading channel 206. Similarly, where one wishes to substantially dilute the sample material, e.g., where the reagent is a diluent, one can provide the reagent introduction channel with a much lower flow resistance than the sampling capillary, e.g., 10× lower or more, to achieve an appropriate dilution, e.g., 10 fold or greater. In the case of the device illustrated in FIG. 2A, one must also consider the flow of material into sample loading channel coming from the separation channel 204 via injection channel 208. However, as shown, these channels are provided with a sufficiently high resistance, e.g., through a narrow cross-sectional area and an included viscous separation matrix, so as to substantially negate this flow contribution.

Flow resistance in a channel is typically varied by either altering the cross sectional area of a channel, changing a channel's length, or altering the viscosity of fluid to be moved through the channel, or a combination of any of these. In preferred aspects, flow resistance is altered by configuring the various channels to have different cross sectional areas and/or different lengths. These two parameters are easily considered in the process of fabricating the microfluidic channel networks, e.g., by varying the width or depth of channels and by varying the path of channels to vary their length. In the device shown, the reagent introduction channel is provided with a lower resistance by providing the channel with a substantially larger cross section, as a result of a greater depth and width, as compared to the sampling capillary. These dimensions, when combined with the channels length, provide for an appropriate selected mixing ratio, e.g., 3:1 reagent to sample material as shown, for the sample material and reagent.

Once sample material, and optionally mixed reagent, is loaded into the sample loading channel 206, a portion of the sample material is moved, or injected, from the sample loading channel, through injection channel 208, and into the separation channel 204. Injection of the portion of sample material into the separation channel may be accomplished by applying a pressure differential through injection channel 208 to move sample material into the separation channel. Alternatively, and preferably, a portion of the sample material (or mixture of sample material and reagent), is injected by applying a voltage differential across the crossing channel to electrokinetically inject the sample material into the separation cannel. In either case, application of a motive force, e.g., electrical current or pressure differential, is typically applied through reservoirs 220 and 226. For example, for a preferred electrokinetic injection, a current is applied between the sample loading channel 206 and the separation channel 204 by applying a voltage gradient between reservoirs 220 and 226, which generates a current through channel 216, a portion of channel 206, and channel 208. The established current then electrokinetically moves sample material from the sample loading channel 206 into injection channel 208 and across separation channel 204 at the intersection of these channels.

Following injection of the sample material through the intersection of injection channel 208 and separation channel 204, an electrical current is applied through the length of the separation channel to electrokinetically move the sample material at the intersection into and through the separation channel. In preferred aspects, a slight current is supplied back through the portions of channel 208 that meet with separation channel 204, in order to push back sample material from the intersection. This improves separation efficiencies by eliminating substantial leakage that can contaminate the separation run. As the sample material is electrophoresed through the sample matrix in the separation channel, it is separated into fractions, e.g., that differ based upon their molecular weights.

Once the separation of the sample material is completed, or in some cases, while the separation is being carried out, a subsequent sample material may be loaded into the sample loading channel by contacting the external pipettor 214 with a subsequent source of sample material and drawing the sample into the sample loading channel. This subsequent sample material is then injected and separated as described above.

Figure 3A:
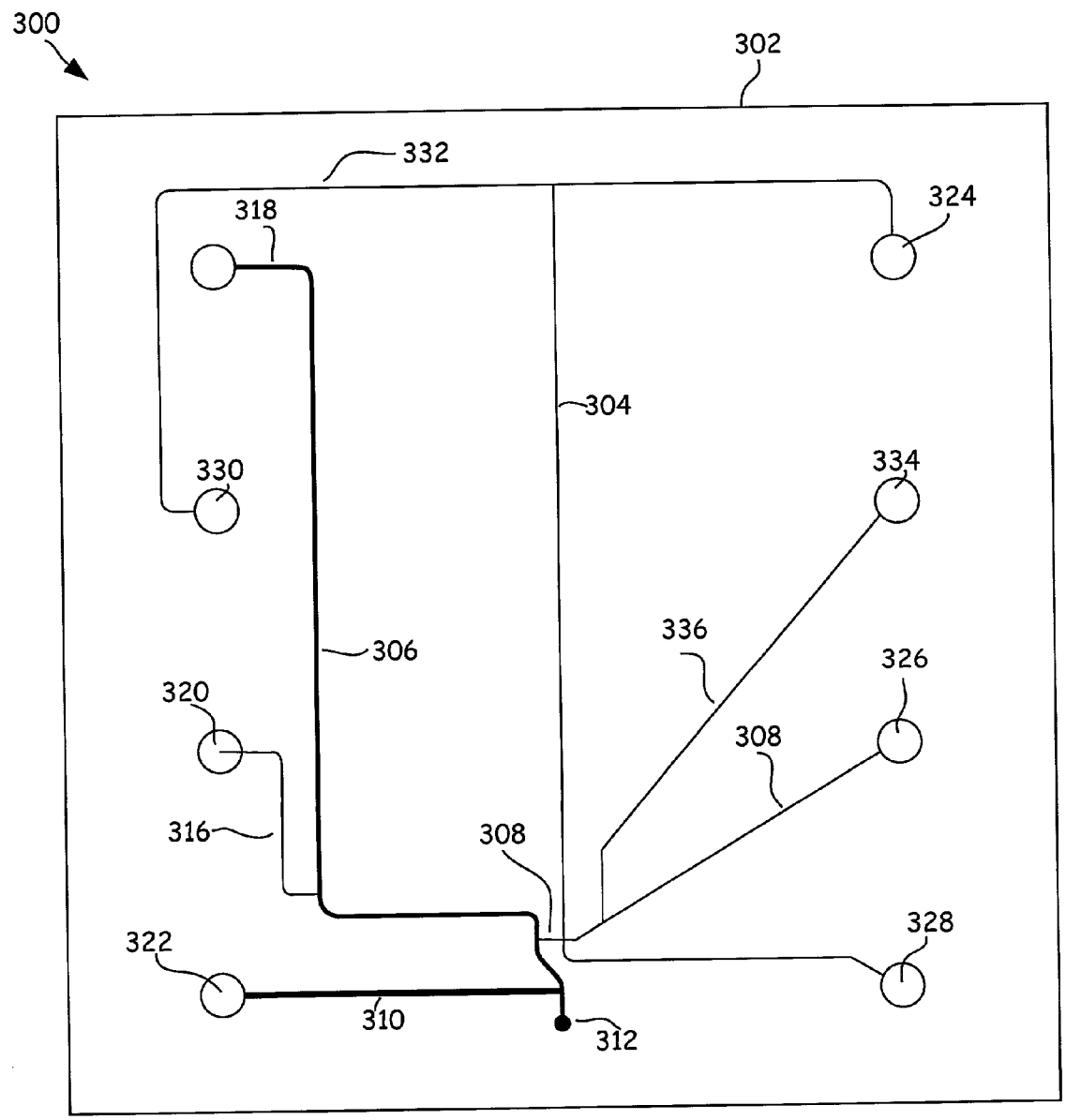
FIG. 3A is one alternate channel layout for performing separations based analyses according to the present invention.
Figure 4:
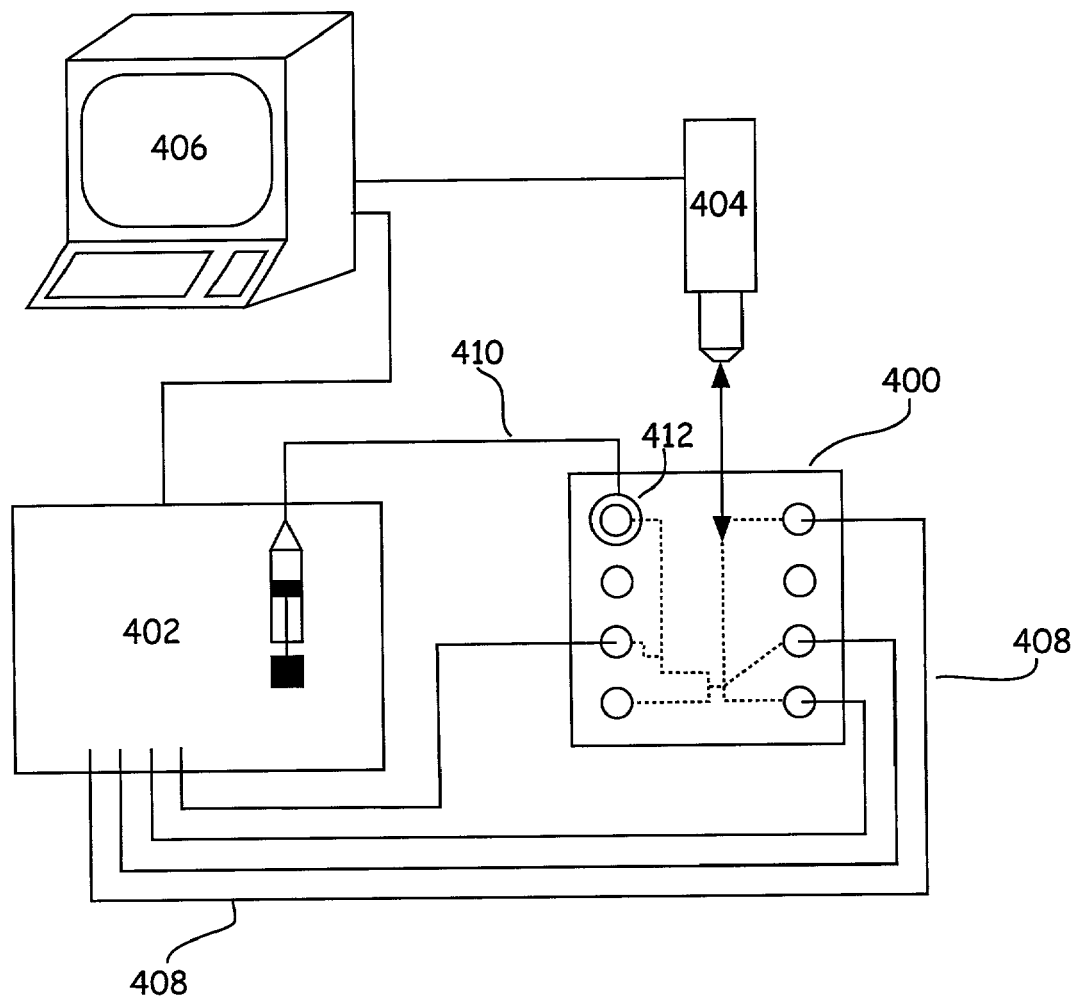
FIG. 4 is a schematic representation of an overall system for performing high throughput separations based analyses in accordance with the present invention.

As shown in FIG. 3A, in some cases an additional reservoir 230 may be provided connected to the separation channel 304, e.g., via channel 332, to provide additional volume of separation matrix to the separation channel 304. This matrix is then directed into the separation channel 304 between separation runs, either in the context of sample loading (as described with respect to at least one aspect of the invention), or as a separate process step in repeated analyses. This additional reservoir is typically connected, e.g., via an appropriate channel 332, at a point in the separation channel that is proximal to one or the other end of the separation column, e.g., at the buffer well 328 end or the waste reservoir 324 end (as shown in FIG. 2). In preferred aspects, the additional reservoir is connected proximal to the waste reservoir end and the matrix is drawn into the separation channel to displace only a small portion of the separation matrix in each sample loading step. Specifically, the bulk loading of the sample material draws a small amount of separation matrix out of the separation channel and into the sample loading channel where it is washed away. A like amount of matrix is then drawn into the separation channel from the matrix reservoir. The use of a matrix reservoir separate from the buffer and waste reservoirs 228 and 224, respectively, provides a source of matrix that is not contaminated with materials from previous separation operations, e.g., sample materials, ions, impurities, etc.

Additional reagent reservoirs, e.g., reservoir 334 is also optionally provided for adding additional reagents that are to be routinely used throughout a particular analysis, e.g., standard separation ladder for calibration, etc. As shown, reservoir is coupled to the injection channel 308 via a reagent introduction channel 336, allowing this reagent to be separately and independently injected into the separation channel, as opposed to being mixed with sample material.

Figure 3B:
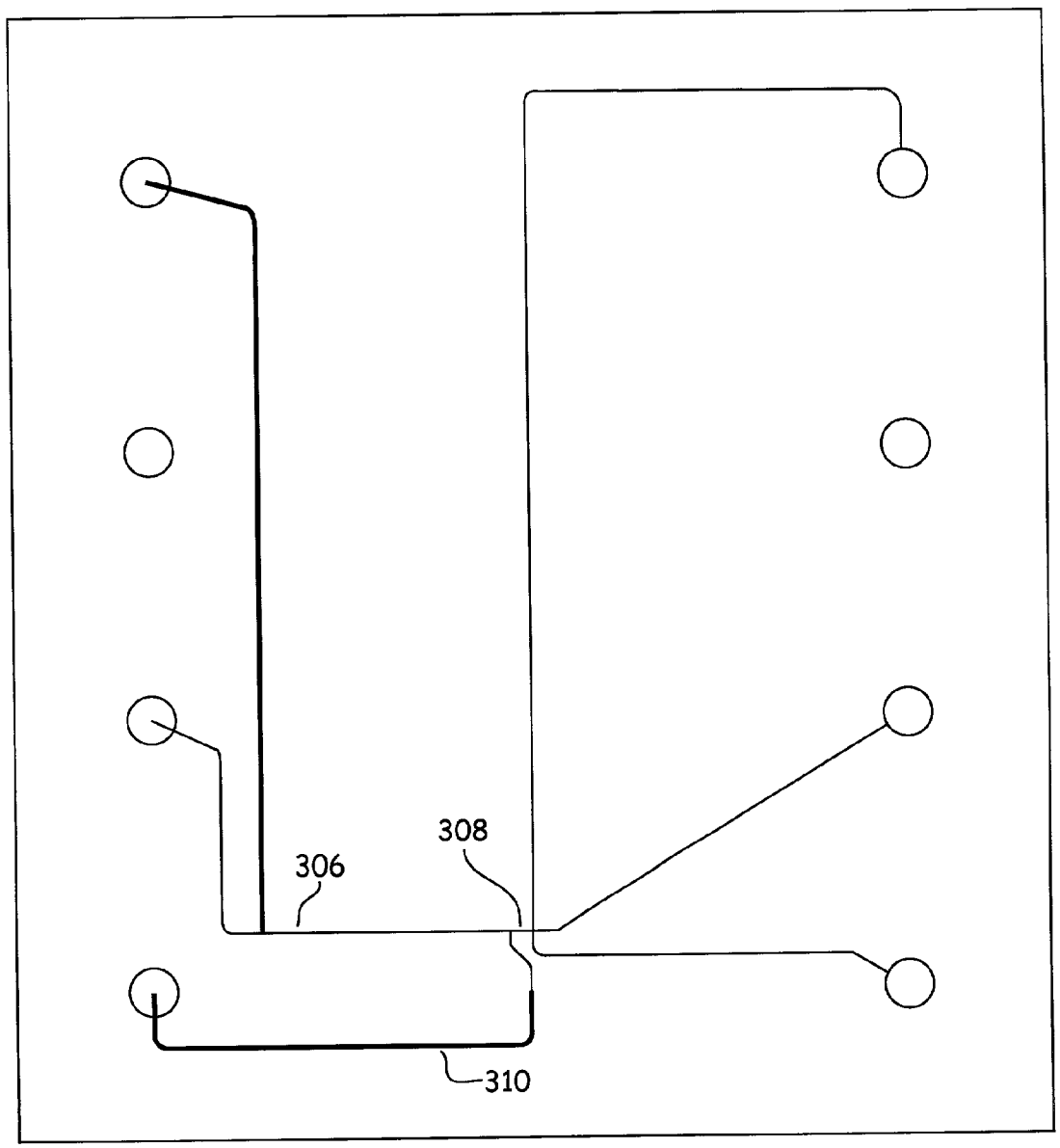
FIG. 3B illustrates one preferred channel layout for performing separations based analyses.
Figure 3C:
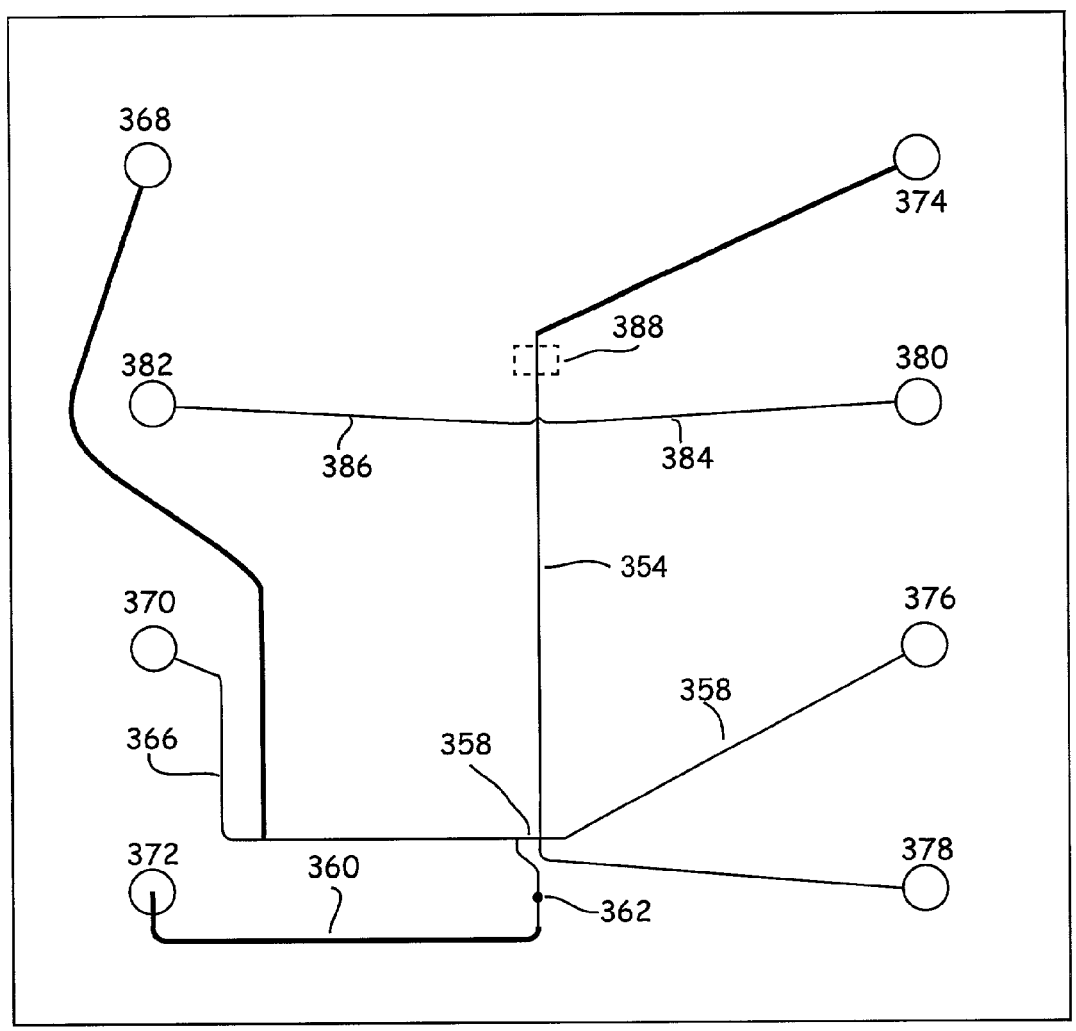
FIG. 3C illustrates a preferred channel layout for carrying out separations based analyses that incorporate a post separation reaction step.

FIG. 3B illustrates an improved channel layout for performing separations based analyses according to the present invention. In particular, in some cases, the existence of a sharp bend in the loading channel 206 shown in FIG. 2A, close to the injection intersection can give rise to aberrations in the way materials and/or electric fields flow through that loading channel and are thus injected into the separation channel. In particular, it has been determined that injection of large molecular weight DNA gave inconsistent results in the channel layout illustrated in FIG. 2A. Without being bound to a particular theory of operation, it was believed that such inconsistencies arose from the sharp bend in the loading channel 206 as shown in FIG. 2A, adjacent to the injection point. The sharp bend yields substantially non-uniform electric fields during the injection process that are high on the inside track of the corner and lower on the outer track. This was believed to be the cause of the inconsistency. In particular, slight differences in sample conductivity between different samples change the field strength around the bend. The dispersion around the bend, as well as the dispersion caused by the differential electrophoretic mobility convolves to cause the non-uniform injection of slower moving, e.g., larger components.

In order to remove these inconsistencies, a modified channel layout was fabricated (see FIG. 3B) in which the loading channel 306 is provided in line (colinear) with the injection channel 308. Maintaining a straight injection channel between the sample loading channel and the separation channel yielded substantially improved consistency with respect to these larger molecular weight species. The alternate design also orients the reagent introduction channel 310 such that the flowing reagents from that channel sweep across the capillary junction/port 312, to avoid aggregation of material within any dead volume of that junction, and to facilitate mixing of reagents coming in from the reagent introduction channel 310 with the material being brought in from the pipettor element. This results in less cross-over contamination among samples brought in through the same capillary element.

FIG. 3C shows a channel layout that is employed in a separation operation where post separation reaction is carried out, e.g., as used in a protein separation, as noted above. As shown, the device is similar in layout to the device shown in FIG. 3B. In particular, the device includes a loading channel 356 that is again, colinear with the injection channel 358, and includes reagent introduction channel 360 oriented such that the flowing reagents from that channel sweep across the capillary junction/port 362. Separation channel 354 is intersected by diluent channels 384 and 386 just upstream of the detection zone 388. These diluent channels are coupled, at their opposite ends, to reservoirs 380 and 382, respectively. As shown in the figure loading channel 356 is detoured around reservoir 382, in order to avoid crossing diluent channel 386. In operation, the device shown in FIG. 3C functions in the same fashion as that shown in FIG. 3B, with the exception that a diluting voltage is applied to reservoirs 380 and 382, in order to drive diluent into the separation channel 354, e.g., diluting ions and/or fluids, in order to achieve the desired result at the detection point. In the case of protein separations, this results in a dilution of the separation buffer to below the critical micellar concentration, resulting in a decrease in background signal levels associated with excessive detergent micelles. The principles and operation of this assay are described in detail in published PCT Application No. WO 00/46594, previously incorporated herein by reference in its entirety for all purposes. As with the device shown in FIG. 2A, during separation, a voltage is applied between reservoirs 378 and 374 in order to drive the electrophoretic separation in separation channel 354.

As shown, the device in FIG. 3C provides nanoliter scale sample access using a fused silica capillary sampling element. As with the devices described above, a single vacuum applied to, e.g., reservoir 324, results in the simultaneous dilution of sample material and mixture with marker compounds. The sample is then electrokinetically injected into the separation channel that includes the separation matrix, including SDS, e.g., 9 mM, and a fluorescent associative dye, see WO 00/46594. The SDS is then diluted out prior to detection.

Figure 3D:
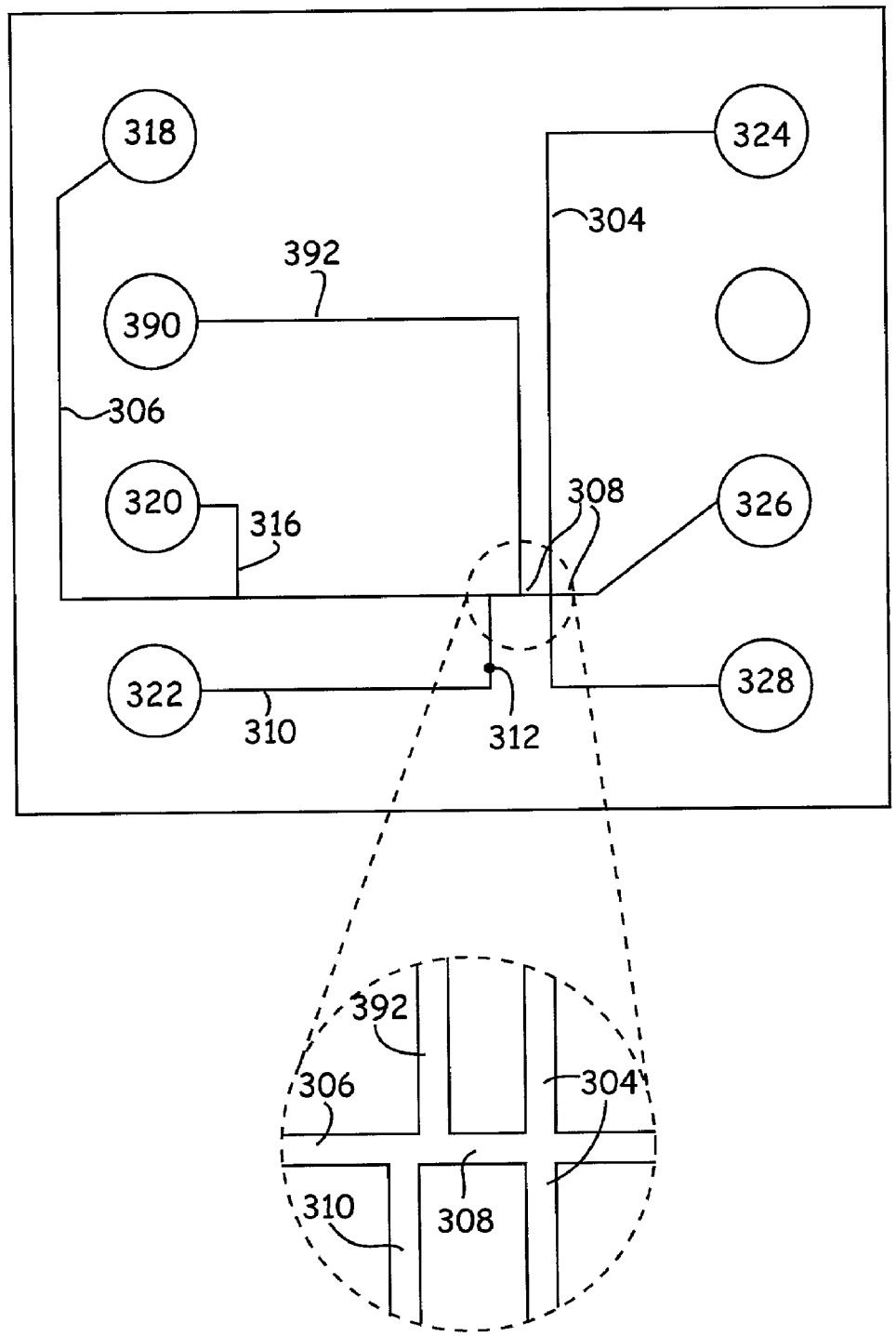
FIG. 3D illustrates a further alternate channel layout for performing separations based analyses.

A further channel layout option is illustrated in FIG. 3D. As shown, the layout in FIG. 3D includes all of the same channels as shown in the device of FIG. 3B, although they may be in slightly different locations. In addition, however, the device shown in FIG. 3D includes an additional channel for use in managing the pull-back step of an injection and separation. The addition of this channel allows for faster loading of subsequent samples, e.g., during a prior separation step, without risk of sample carry-over contamination. Similar channels in each of the devices illustrated in FIGS. 3B and 3D are identified with the same reference numerals.

In operation, the device in FIG. 3D functions in substantially the same fashion as the device in FIG. 3B. In particular, a sample material is drawn into the channels of the device through an external pipettor via port 312. The process of drawing sample material into the device, e.g., by applying a vacuum to reservoir 318) also draws additional reagent from reservoir 322 via reagent introduction channel 310 into sample loading channel 306, where the reagent mixes with the first sample material. An electric current is applied between reservoir 320 and 326 to load sample material into the injection intersection of channel 308 and separation channel 304. Once loaded, the sample material is injected into channel 304 and separated by applying a current between reservoirs 328 and 324. During separation, a slight pull-back current is applied to move the sample material in either side of channel 308 away from the injection intersection, to avoid leakage of sample into the separation channel during separation. In the device shown in FIG. 3D, the pull back is directed back toward reservoir 326 and reservoir 390, via channel 392 (as opposed to back toward reservoir 318 in the device of FIG. 3B). By shunting off pulled-back sample material, one removes it from the sample loading chanel 306, where it could potentially mix with subsequent sample materials and contaminate subsequent runs. Further, as is illustrated in the expanded view of the injection intersection, channel 392 is provided intersecting the injection chanel slightlycloser to the injection intersection that the junction of channels 310 and 306. This allows one to load a subsequent sample material during a pull-back step without the new sample material and the pulled back material ever crossing paths and mixing. Thus, the pull-back path along channel 392 is different, i.e., it does not traverse the same flow path at the same time and spaced apart from the initial sample loading path along channel 306.

IV. Matrix Maintenance and/or Replacement

Bulk loading of sample material without displacing the separation matrix within the separation channel is a significant advantage of the present invention over conventional capillary methods, as well as previously described microfluidic methods. Specifically, by being able to bulk load sample material, as described above, one can significantly decrease the amount of time required for sample loading over electrophoretic loading methods. Additionally, bulk loading by pressure based methods provides speed of loading without the adverse effects of electrophoretic biasing of sample materials, e.g., a pre-separation, before they are injected into the separation conduit.

As described above, the present invention also permits the bulk loading of sample material without causing excessive displacement of the separation matrix. This would be substantially impossible in conventional capillary systems where any sample material bulk flowed into a capillary would necessarily displace a similar volume of separation matrix. Similarly, in microfluidic devices previously described for performing separation applications (see, e.g., Woolley and Mathies, Proc. Nat'l Acad. Sci. USA, 91:11348–11352(1994)), electrophoretic sample loading was used. In these previously described systems, if a sample were pressure loaded, it would substantially disrupt and displace the separation matrix within the separation channel portion of the device.

In the devices of the present invention, displacement of the separation matrix during bulk sample loading is typically carried out by providing a sufficient flow resistive barrier between the sample loading conduit and the separation conduit. This barrier may be embodied in the configuration of the separation channel as a whole, e.g., providing the separation conduit with a sufficiently high flow resistance to substantially resist bulk flow pressures in the sample loading channel, either positive or negative. Alternatively, the barrier is provided in an injection conduit that links the separation conduit and the sample loading conduit. In particular, the injection conduit that links the sample loading conduit and the separation conduit may be provided with a sufficiently high flow resistance to resist bulk flow between the sample loading and separation conduits.

As noted herein, flow resistances in channel structures are typically varied by altering the cross-sectional area of the channel and/or varying the channel's length, where a smaller cross-sectional area or longer channel length will give rise to a higher flow resistance. Variation of channel lengths typically involves simply altering the channel's course to increase or decrease its length. Similarly, channel cross-sectional areas are typically varied by fabricating the channels shallower, deeper or wider. Advantageously, one can substantially alter the bulk flow or hydrodynamic resistance of a channel, without substantially altering the electrical resistance of that channel, which electrical resistance will affect the amount of current that is passed through the channel, e.g., in electrophoretic injection and separation within the devices described herein. In particular, in microscale channels having aspect ratios (width:depth) of greater than about 5, the hydrodynamic resistance of the channel is a function of the cube of the channel depth, while the electrical resistance is related linearly to the channel depth. Thus, a ten fold reduction in channel depth results in a ten-fold reduction in electrical resistance, but a thousand-fold reduction in hydrodynamic resistance. Taking advantage of this property allows one to significantly increase the hydrodynamic resistance within the injection channel 208 and separation channel 204, while not substantially increasing the electrical resistance through those channels.

In this aspect of the invention, the sample material is bulk loaded without substantially displacing the separation matrix. Typically, the separation matrix is not substantially displaced if less than 10% of the matrix originally present in the separation conduit is displaced, e.g., removed from the separation conduit, during the process of loading a particular sample material, typically less than 5% and preferably less than 1% of the separation matrix is displaced.

In order to accomplish bulk fluid loading in the sample loading channel, while achieving the above-described minimal displacement of matrix in the separation channel, the fluid path that leads into and/or through the separation channel from the sample loading channel is typically provided with a flow resistance that is some selected level higher than the resistance to flow within the sample loading channel into the point of connection. In the case of the device illustrated in FIG. 2, the resistance of separation channel 204, as well as of the small segment of injection channel 208 that connects sample loading channel 208 with separation channel 204, is significantly higher than the resistance of the fluid path from he sample material to the fluid junction of channel 208 and channel 206 (which includes capillary 214 and a portion of sample loading channel 206). Typically, the ratio of these flow resistances (as based upon fluid having the same viscosity) is preferably greater than 2:1 (separation channel: sample loading channel), more preferably, greater than 5:1, and often greater than 10:1 or even higher. Of course, when a viscous separation matrix is introduced into the separation channel, it results in a substantially higher level of flow resistance in the separation channel.

In some cases, it may be desirable to displace some larger or selected portion, yet not the entire separation matrix within the separation conduit. In particular, it is sometimes desirable to replace the separation matrix used in a separation operation, to eliminate cross-contamination between runs for separation of different samples. In such cases, the present invention is also very useful in that it can permit a desired level of matrix displacement during sample loading, without displacing the entire or even a substantial portion of the separation matrix.

Selected displacement of a portion of the separation matrix may be accomplished by a number of methods. For example, a positive pressure may be applied to the reservoir that contains the separation matrix to force new separation matrix into the separation conduit and concurrently displace a portion of the separation matrix that was already within the separation conduit. In preferred aspects, however, the separation matrix is partially displaced during the sample loading process using, at least in part, the same forces used to bulk load he sample material. In particular, and with reference to FIG. 2, when a vacuum is applied to waste reservoir 218 to draw sample material into the sample loading channel 206, the negative pressure also draws a portion of the sample matrix into the sample loading channel 206 from the separation channel 204 via injection channel 208. The displaced matrix is back filled by the separation matrix disposed in one of the reservoirs coupled to the separation channel, e.g., reservoir 224, or an additional matrix storage reservoir, e.g., reservoir 230, that is separate from waste reservoir 224.

In more preferred aspects, the amount of matrix displacement is kept to a selected portion of the total matrix within the separation channel. In particular, as above, when a portion of the matrix is desired to be displaced in each sample loading step, such portion typically includes less than 90% of the separation matrix originally disposed in the separation conduit, more often, less than 75%, preferably less than 50% more preferably less than 20% and still more preferably less than about 10%, 5% or even 1%.

Controlling the relative level of matrix displacement is generally accomplished by varying the relative level of flow resistance between the sample loading channel 206 and the separation channel 204. Specifically, one can vary the flow resistance of the separation channel so that a pre-selected amount of matrix will be displaced under selected sample loading conditions. As noted repeatedly herein, controlling flow resistance of channels is typically accomplished by varying one or more of the cross-sectional area or the length of a given channel. In the case of the device illustrated in FIGS. 2 and 3, the separation channel is provided as a shallower and/or narrower channel as compared to the sample loading channel, to give it a substantially higher flow resistance. This higher hydrodynamic or flow resistance configuration, when combined with the higher viscosity of the separation matrix disposed in the channel yields a substantially reduced flow of material from the separation channel into the sample loading channel under an applied vacuum. As noted above, this increased flow resistance yields only a moderate increase in electrical resistance. The relative flow resistances under these conditions are readily calculated based upon well known fluid mechanics principles which take into account the properties of the fluid, e.g., viscosity, as well as the dimensions, e.g., length and cross sectional area, of the channels through which the fluids are being flowed.

IV. Integrated Reagent Mixing

As noted above, the present invention also provides for the addition and mixing of additional reagents as an integral step to the sample loading process. In particular, when performing conventional capillary based experimentation, e.g., capillary electrophoresis, any reagents that are required or even desired to be introduced into the analysis were required to be introduced to the sample material prior to the sample loading step. In high throughput applications, this additional step can add significant slow-down and a substantial increase in the cost of fluid handling equipment for carrying out the addition. In accordance with the present invention, a reagent introduction/mixing step is integrated into the bulk sample loading step by connecting a source of the reagent material to the sample loading conduit such that the reagent is introduced into the sample loading conduit concurrently with the sample material.

For example, as noted above with respect to the discussion of FIG. 2, a reagent reservoir 222 is optionally provided integrated within the body structure 202 of a microfluidic device 200. The reagent reservoir 222 is fluidly coupled to the sample loading channel 206 via reagent introduction channel 210. When sample material is being bulk flowed into the sample loading channel 206, an appropriate motive force is also applied to force the reagent material in reservoir 222 through channel 210 and into sample loading channel 206. The motive force typically depends upon the nature of the force used to bulk load the sample material into the sample loading channel 206. For example, where sample material is loaded into sample loading channel 206 via vacuum applied at, e.g., waste reservoir 218, that same applied vacuum typically draws reagent from reservoir 222 into the sample loading channel 206. Alternatively or additionally, a positive pressure may be applied to reagent reservoir 222, which pushes the reagent into the sample loading channel, either alone or in conjunction with an applied vacuum at reservoir 218. Controlling positive and/or negative pressures at multiple reservoirs in an interconnected microchannel structure as illustrated in FIG. 2 was described in U.S. Patent Application No. 60/184,390, filed Feb. 23, 2000, and which was previously incorporated herein by reference in its entirety for all purposes.

Since, in preferred aspects, an applied vacuum is used to draw sample material, and at least in part, reagent material into the sample loading channel, the flow resistance of the capillary element 214 and the reagent introduction channel 210 are typically configured to provide for an appropriate mixing ratio of sample and reagent flowing through those channels. Specifically, and as set forth above, the relative resistances of the channels through which materials are being drawn into a common channel, e.g., the capillary element and the reagent introduction channel, are selected to provide a desired ratio of sample and reagent flowing into the sample loading channel. This selection typically involves fabricating the channels with appropriate cross sectional dimensions and/or lengths to yield the resistance that is desired.

In the case of a separations based analysis, the additional reagent supplied via the integrated reagent reservoir typically includes at least one internal standard, e.g., a molecular weight marker compound. By integrating the mixture of the internal standard with the sample material, it eliminates the need for a separate standard analysis step, which can vary over a separate sample analysis. For example, in conventional slab gel electrophoresis, an entire lane of the gel is generally devoted to running a set of molecular weight standards against which samples are measured. This integrated approach also eliminates the need to mix internal standards with the sample material in a separate vessel, e.g., a multiwell plate or test tube, as is often done in typical capillary based separation methods.

The present invention is further illustrated with reference to the following non-limiting examples.

V. EXAMPLES

The principles of the present invention are illustrated in the following examples.

Example 1

Chip Design and Fabrication

A microfluidic device having a channel and reservoir configuration illustrated in FIG. 2 was fabricated from a pair of planar glass substrates. In particular, a first substrate was etched to provide the various channels of the device. Channels 206 and 210 were etched to a depth of approximately 20 µm, with channel 206 having a width (at the top of the channel) of approximately 90 µm while channel 210 had a width of approximately 165 µm. Channel 204, 208 and 216 were etched to a depth of approximately 7 µm and widths of approximately 24 µm. The overall length of the separation channel 204 was 56 mm, while the injection channel 208 was 15.6 mm in overall length which included a 0.5 mm segment connecting the separation channel to the sample loading channel 206. The sample loading channel 206 had an overall length of 39.6 mm, while the reagent introduction channel 210 had a length of 13.2 mm and the electrical connecting channel 216 was 8.9 mm long. Reservoirs were then drilled into the substrate at the termini of the channels. A planar substrate was overlaid and thermally bonded to the first substrate to seal the channels and provide a bottom surface for the reservoirs having a single small hole drilled through it having the same dimensions as the outer diameter of the capillary. The hole was positioned to communicate with the end of the sample loading channel 206. A capillary was then inserted into the hole and attached with an adhesive.

Example 2

Serial Separations-Based Analysis

The device shown in FIG. 2 was used to perform a number of serial DNA separations by bulk loading sample material into the sample loading channel, injecting a small fraction of that material into the separation channel that included a separation medium, and electrophoretically separating the material.

All reagents were taken from a DNA 7500 LabChip® kit, commercially available from Agilent Technologies. The separation medium included a mixture of a sieving polymer solution and DNA intercalating dye. Internal DNA marker standards (DNA Markers) contained a 15 bp and 2000 bp DNA fragments, each at a concentration of 5 ng/µl. The DNA ladder, used to generate a standard curve against which sample data was measured, included fragments of 50 bp, 100 bp, 500 bp, 700 bp and 1000 bp, where each fragment was present at a concentration of 4 ng/µl.

The microfluidic device was prepared by adding 25 µl of the separation medium to reservoirs 220, 224, 226 and 228 (as shown in FIG. 2). These wells were each pressurized at 3 psi for 2 minutes. An additional 25 µl of separation medium was then added to the above reservoirs. Fifty µl of the DNA Marker reagent was then added to reservoir 222. The open end of the capillary element 214 was then inserted into a buffer well on a microwell plate, and a vacuum of 2 psi was applied to reservoir 218. The vacuum draws the buffer and DNA markers into the loading channel 206. After 1 minute of applying vacuum, the chip is ready for use in analysis.

Figure 5:
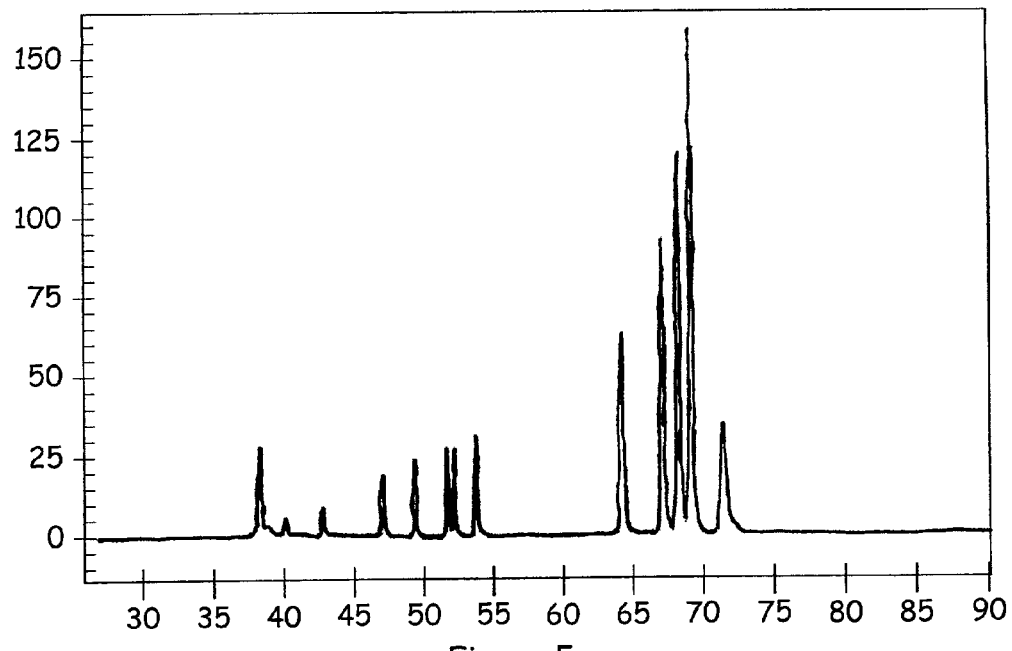
FIG. 5 is a plot of fluorescence versus time during a separation based analysis of ΦX174/Hae III DNA using the devices and methods of the present invention.

DNA containing samples were placed into a 96 well plate and placed upon a x-y-z robotic arm that positions the plate relative to the capillary element, such that the capillary can be immersed in each of the wells of the plate, if desired. Sample materials were then drawn into the capillary element and sample loading channel, by applying a vacuum of 2 psi. 2000 V was applied across injection channel 208 for 5 seconds to force the DNA sample across the intersection with the separation channel 204. A slight pinching current (0.5 µA in each channel portion) was applied for 2 seconds in separation channel to avoid spreading of the sample plug at the intersection, and 1500 V was then applied along the length of the separation channel to move the DNA sample along the separation channel. Concurrently, a slight pullback current (0.1A in each direction) was applied to the portions of the injection channel 208. Multiple separations were run on samples of ΦX174/Hae III DNA. A representative electropherogram from these runs is shown in FIG. 5, which illustrates a rapid (approximately 75 seconds separation time), high-resolution separation. The separation was repeated approximately 100 times with no appreciable degradation in separation resolution.

Example 3

Post Separation Dilution for Protein Separations

The device shown in FIG. 3C was used to perform a protein separation where a post separation dilution operation is performed prior to detection. The device was loaded with a separation matrix that was made up of 3.25% polydimethylacrylamide co-acrylic acid with 0.25% SDS and syto 60 dye 1t 4 µM, in 0.12 mM tricine buffer. The separation matrix was loaded into reservoirs 370, and 374–382 and these wells were pressurized using a syringe for 4 minutes each to drive the matrix through the channels of the device. The matrix mixture in wells 380 and 382 was removed and replaced with matrix that lacked SDS and dye.

The sample for separation was a Bio-Rad standard protein ladder (#148–2015) that had been diluted 3× in PBS. Fifty µl of the diluted ladder was mixed with 25 µl of sample buffer (4% SDS, 10 mM tricine, 3.5 mM Tris) and heated to 100 ° C. for 5 minutes. After heating, the samples were diluted with 150 Ml of water and the samples were loaded into wells of a 96 well plate.

Figure 6:
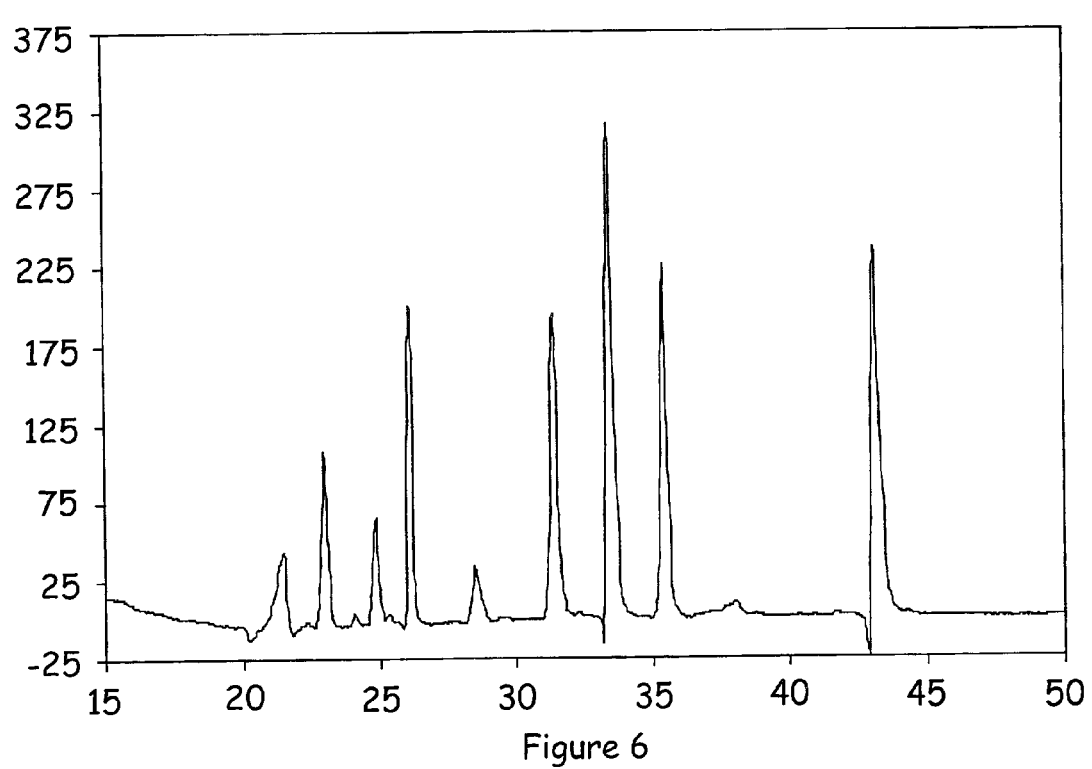
FIG. 6 is a plot of fluorescence versus time during a separation of a standard protein ladder that includes a post separation dilution step, using the methods and systems of the invention.

The chip was operated by placing the sampling capillary's end into the well of the 96 well plate and applying a vacuum at 5 PSI to well 368 to draw the sample from the well through the capillary into the chip. During sample loading, the sample is diluted 1:1 with water present in well 372. The sample material was then loaded into the injection intersection of channels 358 and 354 by applying 2000 V between wells 370 and 376. The sample was then injected by applying 2350 volts between reservoirs 378 and 374, with a pull back current of −0.3 µA and −0.1 µA being applied to wells 370 and 376, respectively. The separation continued at 2350 volts applied between well 378 and 374 with 2550 volts being applied to the destain wells 380 and 382 to drive the diluent into the separation channel, while maintaining a pullback at reservoir 376 of −0.05 µA. This results in a destaining ratio of approximately 9:1. The fluorescent peaks were detected at the detection zone 388. The plot of fluorescence vs time is shown in FIG. 6, indicating high resolution, baseline separation of all of the ladder components.

All publications and patent applications are herein incorporated by reference to the same extent as if each individual publication or patent application was specifically and individually indicated to be incorporated by reference. Although the present invention has been described in some detail by way of illustration and example for purposes of clarity and understanding, it will be apparent that certain changes and modifications may be practiced within the scope of the appended claims.

What is claimed is:

1. A method of separating one or more sample materials into a plurality of fractions, comprising;
    providing a system comprising:
        a separation channel having a separation matrix disposed therein,
        a source of additional separation matrix in fluid communication with the separation channel,
        an injection channel in fluid communication with the separation channel at an intermediate point along the injection channel, and
        a sample loading channel in fluid communication with the injection channel, a source of a first sample material, and a source of a reagent;
    transporting the first sample material and the reagent into the sample loading channel, wherein the first sample material and the reagent form a mixture;
    injecting a portion of the mixture from the sample loading channel, through the injection channel, into the separation channel;
    separating the first sample material within the mixture into a plurality of fractions;
    displacing a portion of the separation matrix from the separation channel after separating the first sample material into a plurality of fractions; and
    transporting a second sample material into the sample loading channel, wherein the force used to transport the second sample material into the sample loading channel displaces the portion of the separation matrix from the separation channel and replaces the displaced portion of the separation matrix with additional separation matrix.

2. The method of claim 1, wherein the sample loading channel comprises a loading end and a waste end, the loading end being contacted with a source of the first sample material, and further comprising applying a first pressure difference across the sample loading channel to move the first sample material into the loading end of the sample loading channel and toward the waste end of the sample loading channel.

3. The method of claim 2, wherein a negative pressure is applied to the waste end of the sample loading channel to supply the first pressure difference across the sample loading channel.

4. The method of claim 2, further comprising applying a second pressure difference across the separation channel to transport an amount of separation matrix into the separation channel from the source of additional separation matrix after the first sample material is separated into a plurality of different fractions.

5. The method of claim 2, wherein the injection channel and the separation channel are in fluid communication at a first fluid junction, and further comprising moving a portion of the first sample material in the injection channel through the first fluid junction and into the separation channel.

6. The method of claim 5, wherein the step of moving a portion of the first sample material through the first fluid junction further comprises applying a pressure differential across the injection channel.

7. The method of claim 5, wherein the step of moving the first sample material through the fluid junction further comprises applying a voltage difference across the injection channel.

8. The method of claim 7, wherein the step of separating the first sample material comprises applying a voltage difference across the separation channel, to electrophoretically separate the first sample material into different fractions.

9. The method of claim 1, wherein less than 10% of the separation matrix in the separation channel is displaced during the step of injecting the first sample material into the sample loading channel.

10. The method of claim 1, wherein less than 5% of the separation matrix in the separation channel is displaced during the step of injecting the first sample material into the sample loading channel.

11. The method of claim 1, wherein less than 1% of the separation matrix in the separation channel is displaced during the step of injecting the first sample material into the sample loading channel.

12. The method of claim 1, wherein the separation channel is provided with a higher flow resistance than the sample loading channel.

13. The method of claim 12, wherein the separation channel comprises one or more of a greater length or a smaller cross-sectional area than the sample loading channel.

14. The method of claim 1, wherein the sample loading channel comprises a loading end and a waste end, the loading end being contacted with a source of the first sample material through a capillary element, and further comprising applying a first pressure difference across the sample loading channel to move the first sample material through the capillary element into the loading end of the sample loading channel and toward the waste end of the sample loading channel.

15. The method of claim 1, wherein the sample loading channel is in fluid communication with the source of reagent through a reagent channel, and wherein the reagent channel and the sample loading channel have differing flow resistances.

16. The method of claim 1, wherein the reagent is selected from a standard compound, a diluent, a detergent, or a labeling reagent.

17. The method of claim 1, wherein the sample loading channel has substantially no separation matrix disposed therein.

18. The method of claim 1, further comprising:
transporting the second sample material through the injection channel and into the separation channel to separate the second sample material into a second plurality of different fractions.

19. The method of claim 1, wherein less than 90% of the separation matrix is displaced.

20. The method of claim 1, wherein less than 75% of the separation matrix is displaced.

21. The method of claim 1, wherein less than 50% of the separation matrix is displaced.

22. The method of claim 1, wherein less than 20% of the separation matrix is displaced.

23. The method of claim 1, wherein less than 10% of the separation matrix is displaced.

24. The method of claim 1, wherein less than 5% of the separation matrix is displaced.

25. The method of claim 1, wherein less than 1% of the separation matrix is displaced.

26. The method of claim 1, wherein the separation channel has at least one microscale cross-sectional dimension.

27. The method of claim 26, wherein the separation channel is disposed in a microfluidic device.

* * * * *